US009739696B2

(12) United States Patent
Luzzato et al.

(10) Patent No.: US 9,739,696 B2
(45) Date of Patent: Aug. 22, 2017

(54) FLEXURAL TESTING APPARATUS FOR MATERIALS AND METHOD OF TESTING MATERIALS

(71) Applicant: Apple Inc., Cupertino, CA (US)

(72) Inventors: Victor Luzzato, Taipei (TW); Dale N. Memering, Cupertino, CA (US)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 14/841,652

(22) Filed: Aug. 31, 2015

(65) Prior Publication Data
US 2017/0059463 A1    Mar. 2, 2017

(51) Int. Cl.
*G01N 3/20*    (2006.01)
*G01N 3/24*    (2006.01)

(52) U.S. Cl.
CPC  *G01N 3/20* (2013.01); *G01N 3/24* (2013.01)

(58) Field of Classification Search
CPC .................................. G01N 3/20; G01N 3/24
USPC .......................................... 73/760, 849, 852
See application file for complete search history.

(56) References Cited

U.S. PATENT DOCUMENTS

| 3,877,298 | A | * | 4/1975 | Narang | G01N 3/42 |
| | | | | | 73/81 |
| 4,245,496 | A | * | 1/1981 | Napetschnig | G01N 3/44 |
| | | | | | 73/83 |
| 4,277,174 | A | * | 7/1981 | Kleesattel | G01B 11/00 |
| | | | | | 356/626 |
| 4,564,408 | A | * | 1/1986 | Crumbach | B29C 43/021 |
| | | | | | 156/212 |
| 4,596,349 | A | * | 6/1986 | Herten | A41H 37/04 |
| | | | | | 227/119 |

(Continued)

FOREIGN PATENT DOCUMENTS

| CN | 101313224 | 11/2008 |
| CN | 201335849 | 10/2009 |

(Continued)

OTHER PUBLICATIONS

Mason et al., "A Generic Multielement Microsystem for Portable Wireless Applications," Proceedings of the IEEE, vol. 86, No. 8, pp. 1733-1746, Aug. 1998.

(Continued)

*Primary Examiner* — Max Noori
(74) *Attorney, Agent, or Firm* — Brownstein Hyatt Farber Schreck, LLP

(57) ABSTRACT

A material testing apparatus and methods of testing material are disclosed. The material testing apparatus may include a support ring contacting a test material and a moveable contact component positioned adjacent to the support ring. The moveable contact component may include a substantially curved contact surface comprising a radius-varying curvature profile formed between a center and a perimeter of the substantially curve contact surface. The curvature profile may be based on a predetermined deflection-force profile specific to the test material. Additionally, the curvature profile may also be based on the material characteristics of the test material, the physical characteristics of the test material, the physical characteristics of the support ring and/or a testing process performed on the test material.

22 Claims, 18 Drawing Sheets

(56) References Cited

U.S. PATENT DOCUMENTS

| | | | |
|---|---|---|---|
| 4,848,141 A * | 7/1989 | Oliver | G01N 3/405 73/81 |
| 4,887,459 A * | 12/1989 | Thomas | G01N 3/42 73/81 |
| 5,479,827 A | 1/1996 | Kimura et al. | |
| 5,541,525 A * | 7/1996 | Wood | H01L 22/20 257/E21.509 |
| 5,616,857 A * | 4/1997 | Merck, Jr. | G01N 3/42 73/82 |
| 5,891,744 A | 4/1999 | Lowrey et al. | |
| 5,892,157 A | 4/1999 | Syre | |
| 6,191,593 B1 | 2/2001 | Tartagni et al. | |
| 6,485,913 B1 | 11/2002 | Becker et al. | |
| 6,644,160 B1 * | 11/2003 | Boselli | B26D 1/30 248/688 |
| 6,884,641 B2 | 4/2005 | Bruley et al. | |
| 6,955,093 B2 * | 10/2005 | Smith | G01N 3/42 73/830 |
| 7,084,652 B2 | 8/2006 | Guo et al. | |
| 7,267,847 B2 | 9/2007 | Karamuk et al. | |
| 7,521,915 B2 | 4/2009 | Herchen | |
| 7,696,538 B2 | 4/2010 | Lee et al. | |
| 7,733,108 B2 | 6/2010 | Kanev et al. | |
| 7,830,267 B2 | 11/2010 | Veerasamy | |
| 7,968,878 B2 | 6/2011 | Aggarwal et al. | |
| 8,091,437 B2 | 1/2012 | Stumpf | |
| 8,156,794 B2 * | 4/2012 | Konaka | G01N 3/42 702/191 |
| 8,253,425 B2 | 8/2012 | Reynolds et al. | |
| 8,821,965 B2 | 9/2014 | Duerig et al. | |
| 8,938,993 B2 | 1/2015 | Harper et al. | |
| 8,939,037 B2 | 1/2015 | Shah | |
| 2005/0181143 A1 | 8/2005 | Zhang et al. | |
| 2006/0139041 A1 | 6/2006 | Nystrom et al. | |
| 2009/0242457 A1 | 10/2009 | Kou | |
| 2010/0249306 A1 | 9/2010 | Berndt et al. | |
| 2011/0195187 A1 | 8/2011 | Weber et al. | |
| 2012/0275088 A1 | 11/2012 | Huang | |
| 2014/0090480 A1 | 4/2014 | Adams et al. | |
| 2014/0360252 A1 | 12/2014 | Yamamoto et al. | |
| 2015/0070037 A1 | 3/2015 | Pragada et al. | |
| 2015/0268273 A1 | 9/2015 | Pragada et al. | |
| 2015/0327370 A1 | 11/2015 | Prest et al. | |

FOREIGN PATENT DOCUMENTS

| | | |
|---|---|---|
| CN | 101617241 | 12/2009 |
| CN | 102081110 | 6/2011 |
| CN | 104359769 | 2/2015 |
| EP | 1834905 | 9/2007 |
| JP | 2011227814 | 11/2011 |
| WO | WO2012/067126 | 5/2012 |

OTHER PUBLICATIONS

Schlaak et al., "Micromechanical Capacitive Acceleration Sensor with Force Compensation," Micro Systems Technologies 90, pp. 617-622, 1990.

* cited by examiner

FLEXURAL TESTING APPARATUS FOR MATERIALS AND METHOD OF TESTING MATERIALS

FIELD

The disclosure relates generally to a material testing apparatus and more particularly to a flexural testing apparatus designed to stress a material to analyze physical and/or mechanical properties of the stressed material and a method of testing the material.

BACKGROUND

Current electronic devices continue to become more prevalent in day-to-day activities. For example, smart phones and tablet computers continue to grow in popularity and provide everyday personal and business functions to its users. These electronic devices typically include input components, such as buttons or screen displays that may be utilized by a user to interact (e.g., input/output) with the electronic devices. These input components may be formed on and/or integrally with the housing of the electronic device.

To maintain and/or to ensure functionality of the electronic device, input components and the housing of electronic devices may be formed from materials that may with stand conventional wear-and-tear on the electronic device. One material that may be used to form the input components and/or the housing may include the crystalline form of alumina (Al2O3) (e.g., corundum), commonly known as sapphire. Specifically, with unique and beneficial chemical or physical characteristics (e.g., hardness, strength), sapphire has become a viable material to be used in current electronic devices.

To ensure all sapphire material used to form components of the electronic device meet quality control standards and/or will function substantially similar between each individual device, the sapphire material may undergo conventional material testing processes. Such material testing processes may include ring-on-ring material testing or ball-on-ring material testing. These tests may apply a force to the sapphire material until the material flexes or breaks. However, because of the unique chemical or physical characteristics of sapphire material and/or the discrepancies that may form in the material, conventional material testing processes may be inadequate. For example, the ring-on-ring and ball-on-ring material testing processes may only form a contact area on the tested sapphire material where the ring or ball contact the material. As such, the ring or ball may only apply a force in the contact area of the sapphire material during the test. This may result in inaccurate measurements of force required to flex and/or break the sapphire; during testing, the ring or ball may not contact areas of the sapphire in which faults or flaws exist and so the effect of such faults or flaws may not be determined by conventional tests.

SUMMARY

A material testing apparatus comprises a support ring operative to contact a test material, and a moveable contact component positioned adjacent the support ring. The moveable contact component may comprise a substantially curved contact surface defined by a radius varying curvature profile formed between a center and a perimeter of the substantially curved contact surface.

A material testing apparatus comprises a support ring operative to support a first side of a test material and a moveable contact component operative to contact a second side of the test material. The moveable contact component comprises a contact surface having a variably-curved curvature profile configured to entirely contact the test material when a predetermined force is exerted on the test material by the moveable contact component. The moveable contact component may also comprise a cylindrical portion positioned adjacent the contact surface.

A method for testing a test material. The method may comprise positioning a test material on a support ring of a material testing apparatus and moving a contact component of the material testing apparatus toward the test material and the support ring to contact a substantially curved contact surface of the contact component to the test material. The substantially curved contact surface may comprise a variably curved curvature profile based on a deflection-force profile for the test material. The method may also comprise increasing a contact area between the substantially curved contact surface of the contact component and the test material, and deflecting the test material using the contact component. The test material may be deflected to one of a calculated flexion distance for the test material, or beyond the calculated flexion distance for the test material.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates generally to a material testing apparatus and, more particularly, to a flexural testing apparatus designed to stress a material to analyze physical and/or mechanical properties of the stressed material and a method of testing the material.

The material testing apparatus design and/or structure provides a uniform distribution of force over a face of a test material. Specifically, a substantially curved contact surface of a moveable contact component of the testing apparatus includes a unique curvature profile. The unique curvature profile is based on a predetermined, calculated deflection-force profile for the test material (e.g., shape or curvature the test material when it is flexed by the testing apparatus) and/or the type of test (e.g., maximum flexion test, breakage test) being conducted on the test material. By implementing the unique curvature profile for the substantially curved contact surface, the force applied to the test material may be over a greater contact area and/or the contact area of the test material may increase during testing. The larger the contact area of the test material, the more accurate the data regarding the stress applied to the test material. Additionally, the testing apparatus and process of testing material using the testing apparatus can be performed to obtain accurate data regarding the stress applied to the test material, and/or physical or mechanical properties of the test material even when the test material is substantially thin (e.g., less than 0.5 millimeters (mm) and, in some cases, as low as 0.2 mm) and is typically brittle.

These and other embodiments are discussed below with reference to FIGS. 1A-12. However, those skilled in the art will readily appreciate that the detailed description given herein with respect to these Figures is for explanatory purposes only and should not be construed as limiting.

Figure 1:
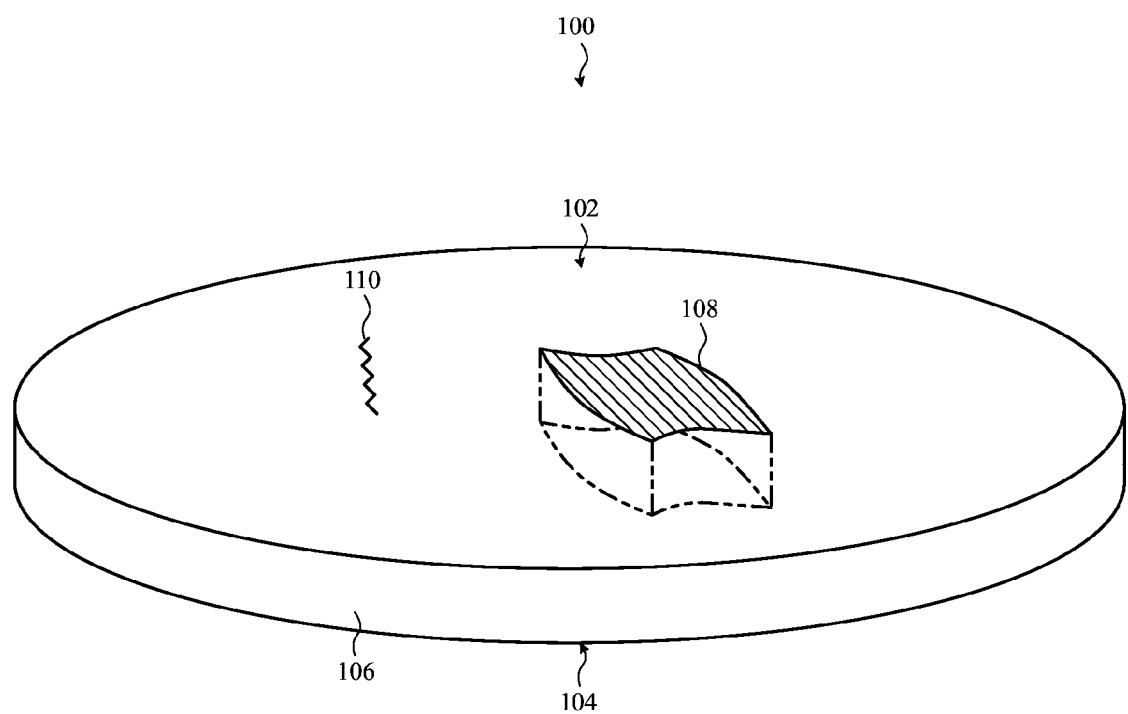
FIG. 1 depicts an illustrative perspective view of a sapphire structure that is processed to form individual sapphire components for electronic devices, according to embodiments of the invention.

FIG. 1 shows an illustrative perspective view of a sapphire structure 100. Sapphire structure 100, as shown in FIG. 1, may be a wafer of artificially grown corundum to be further processed and used in an electronic device. The artificially grown corundum used to form sapphire structure 100 may be grown using any conventional growth process including, but not limited to: hydrothermal growth; vertical horizontal gradient freezing ("VHGF"); edge-defined film-fed growth ("EFG"); horizontal moving growth (e.g., Bridgman growth); and Kyropoulos growth. Sapphire structure 100 may be singulated or otherwise formed into individual pieces or components that may be utilized as a variety of components of many, distinct electronic devices. In non-limiting examples, processed components formed from sapphire structure 100 may include cover glasses, buttons, caps, housings or enclosures and the like for an electronic device. The sample electronic devices may take the form of a tablet computing device, phone, personal digital assistant, computer, wearable electronic device (e.g., smart watch), digital music player and so on.

Sapphire structure 100 may define a top surface 102 and a bottom surface 104 positioned opposite top surface 102. As shown in FIG. 1, sidewall 106 may be substantially perpendicular to both top surface 102 and bottom surface 104. Sapphire structure 100 may include a number of possible plane orientations for the surfaces (e.g., top surface 102, bottom surface 104) of sapphire structure 100. In a non-limiting example, each of the surfaces of sapphire structure 100 may be in alignment with a crystallographic plane orientation determined by the formation of sapphire structure 100. As shown in FIG. 1, top surface 102 may have an A-plane crystallographic orientation, while sidewall 106 may have a C-plane crystallographic orientation. Other examples may have different crystallographic orientations, and so this example is not intended to be limiting. Sapphire structure 100 can be formed to have a thickness as low as approximately 0.2 millimeters (mm), and more specifically, may have a thickness ranging from approximately 0.25 mm to 0.3 mm. As discussed herein, the testing apparatus and process for testing sapphire structure 100 can accurately detect mechanical and physical properties of sapphire structure 100 that are typically brittle and/or thin (e.g., less than 0.5 mm and, in some cases, as low as 0.2 mm). It should be appreciated that ranges given herein are mere examples; the testing apparatus can be used with substrates that are thicker than 0.5 mm, for example. Likewise, although the apparatus is discussed as testing sapphire, other materials can be tested in similar fashion and so test sheets, substrates, materials and the like are not limited to sapphire.

Generally, corundum (e.g., sapphire) is an anisotropic material. As a result, the crystallographic orientation of the surfaces of components made from corundum or sapphire (e.g., sapphire structure 100) may affect the physical properties and/or material characteristics (including strength, ductility, and/or elasticity) of the component. The crystallographic orientation of the various surfaces may be dependent on the growing processes used for creating the corundum of sapphire structure 100 and/or the additional processes (e.g., cutting polishing) used to form sapphire structure 100 and distinct components from sapphire structure 100. For example, the corundum from which sapphire structure 100 is formed may be grown using an EFG growth process. In the growth process, the seed crystal may include a plane orientation to yield corundum that may allow for specific, desired planes to be utilized in components formed from the corundum. By knowing the orientation of the seed crystal used in the EFG growth process and ultimately knowing the crystallographic orientation of the grown corundum, manufactures can cut the corundum in a specific direction to form sapphire structure 100 and subsequent components from sapphire structure 100 with surfaces having specific plane crystallographic orientations or substantially desirable plane crystallographic orientations.

As a result of the various processes performed on the grown corundum to form sapphire structure 100 and/or because of the physical characteristics (e.g., brittleness) of at least some of the crystallographic plane orientations used to from the various surfaces of sapphire structure 100, sapphire structure 100 may include material defects. The material defects formed in sapphire structure 100 may substantially and/or negatively impact the physical and material characteristics of sapphire structure 100, and ultimately, the individual components formed from sapphire structure 100. In a non-limiting example shown in FIG. 1, a material defect may include a material irregularity 108. Material irregularity 108 may be formed in a portion of sapphire structure 100 and may extend through a portion or the entire thickness of sapphire structure 100; the exact size and shape shown is an example and not intended to be illustrative of any particular defect.

Material irregularity 108 may be formed in the corundum that may be processed to form sapphire structure 100. In a non-limiting example, the corundum that may be grown and subsequently cut to form sapphire structure 100 may have initial compositional impurities or powder other than pure alumina. Alternatively, the corundum may experience fluctuations in processing parameters such as temperature, time and/or pressure. As a result, when the corundum is processed and/or grown, the portions of the corundum containing compositional impurities (or subject to such fluctuations) may form material irregularity 108 in sapphire structure 100. The compositional impurities that create material irregularity 108 in sapphire structure 100 may make sapphire structure 100 weaker in the portion including the material irregularity 108 when compared to the remaining portions of sapphire structure 100.

In another non-limiting example, the material defect 108 of sapphire structure 100 may be an over-annealed portion. In the non-limiting example, sapphire structure 100 may undergo an annealing process to strength the material. However, sapphire structure 100 may include a portion that may be over-annealed, e.g., that may be heated to a greater-than-desired temperature and/or not cooled to a desired temperature after heating. Over-annealed portion may affect the physical and material characteristics of sapphire structure 100. In the non-limiting example, an over-annealed portion of sapphire structure 100 may be softer and/or weaker than the remaining portions of sapphire structure 100.

Sapphire structure 100 may also have one or more cracks 110 formed on top surface 102 of sapphire structure 100. Crack 110 may extend partially through sapphire structure 100 or may extend completely through sapphire structure 100. Crack 110 may be formed due to normal wear and tear of sapphire structure 100 and/or from a shock event, such as an impact.

Figure 2A:
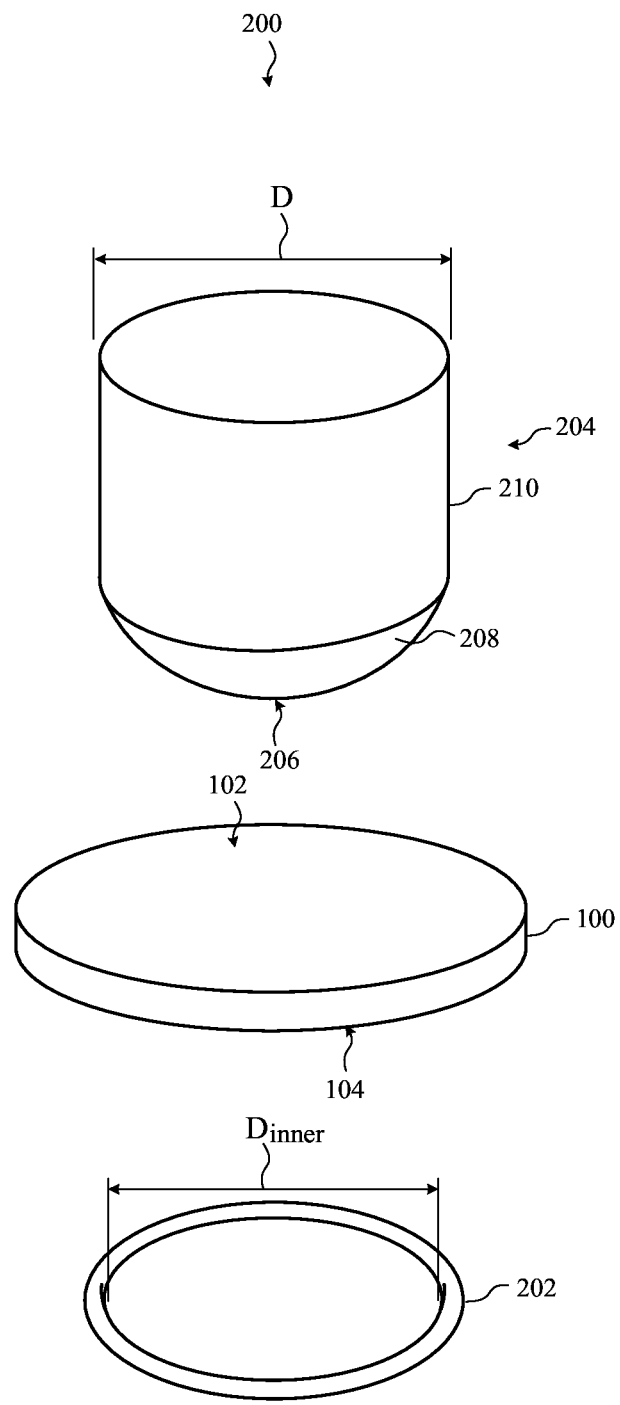
FIGS. 2A and 2B depict illustrative perspective views of a material testing apparatus for testing the sapphire structure of FIG. 1, according to embodiments.
Figure 2B:
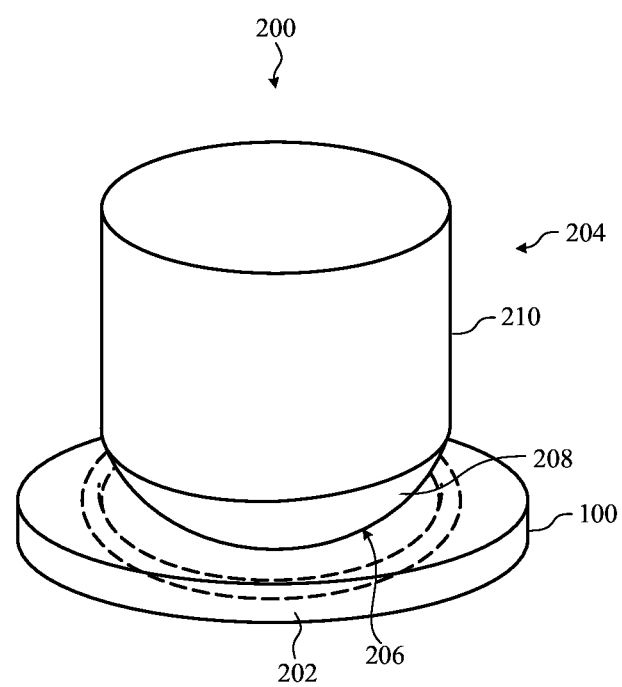

FIGS. 2A and 2B show illustrative perspective views of a material testing apparatus 200 and sapphire structure 100; FIG. 2A shows material testing apparatus 200 and sapphire structure 100 in an exploded view, while FIG. 2B shows material testing apparatus 200 and sapphire structure 100 aligned in an operational position for testing the sapphire structure, as discussed herein.

Material testing apparatus 200 may include a support ring 202 or other suitable support structure. The shape of the support structure may vary between embodiments, but typically matches a shape of the contact surface 206 of a moveable contact component, which is discussed in more detail below. Support ring 202 may contact a test material (e.g., sapphire structure 100) as part of a testing process using material testing apparatus 200, as discussed herein. As shown in FIG. 2B, bottom surface 104 of sapphire structure 100 may rest on, be positioned on and/or be disposed over support ring 202 during the material testing process. Support ring 202 may be substantially circular and/or rounded to ensure support ring 202 contacts sapphire structure 100 and there is no gap or space between support ring 202 and sapphire structure 100. Although shown as substantially circular, support ring 202 may also be substantially flat to provide a uniform contact with sapphire structure 100 during a testing process discussed herein. In a non-limiting example, support ring 202 may be formed from a substantially rigid material that may support sapphire structure 100 without deforming and/or without allowing sapphire structure 100 to move when sapphire structure 100 undergoes the material testing process.

As shown in FIGS. 2A and 2B, material testing apparatus 200 may also include a moveable contact component 204 positioned adjacent support ring 202. Moveable contact component 204 may be positioned above sapphire structure 100 and support ring 202, while sapphire structure 100 may be positioned between moveable contact component 204 and support ring 202. Moveable contact component 204 moves toward and contacts sapphire structure 100 during a material testing process, as discussed herein.

Moveable contact component 204 may be formed from a number of different components. In a non-limiting example shown in FIGS. 2A and 2B, moveable contact component 204 may include a substantially curved contact surface 206, although the contact surface may have other shapes (e.g., cubic, pyramidal, etc.). Substantially curved contact surface 206 of moveable contact component 204 may be positioned adjacent to and/or may contact top surface 102 of sapphire structure 100 opposite bottom surface 104 contacting support ring 202 during the material testing process. Substantially curved contact surface 206 may be formed on a contact portion 208 of moveable contract component 204. As shown in FIGS. 2A and 2B, contact portion 208 may be substantially circular and/or dome shaped.

Further and as discussed herein, substantially curved contact surface 206 including contact portion 208 may have a unique curvature profile 212 (which may correspond to a cross-section) based on a variety of characteristics relating to sapphire structure 100, support ring 202, the specific test to be performed on sapphire structure 100 and so on. For example, the unique curvature profile 212 may have distinct portions having varying radius; that is, one portion of the curvature profile 212 (and so one portion of the contact surface) may be defined by a first radius extending from a centralized point of the contact portion 208, while a second portion of the curvature profile 212 (and so a second portion of the contact surface) may be defined by a second radius from the centralized point, and so on. This centralized point may be the center of a circle defined by the arc segment forming the first portion of the curvature profile 212, for example. The first radius and the second radius may be distinct and/or vary from one another, and the varying radius of the curvature profile 212 may vary on or along substantially curved contact surface 206 as it transitions from a center to a perimeter of contact portion 208. Additional discussion of curvature profiles 212 of varying radii is given herein with respect to FIGS. 9-12. The transition between the first and second portions, and any further portions, of the curvature profile 212 may be smooth such that the surface appears substantially continuous. Alternatively, the transition or transitions between such portions may be abrupt and visible. As yet another option, the curvature profile 212 of the contact portion 208 may vary substantially continuously, such that it forms a parabola.

In non-limiting examples, substantially curved contact surface 206 of moveable contact component 204 may have a diameter (D) equal to or smaller than an inner diameter ($D_{inner}$) of support ring 202. The diameter (D) of substantially curved contact surface 206 may be dependent on, at least in part, the specific test to be performed on sapphire structure 100. For example, and as discussed herein, diameter (D) of substantially curved contact surface 206 may be smaller than inner diameter ($D_{inner}$) of support ring 202 when moveable contact component 204 is utilized in a material testing process that deflects sapphire structure 100 beyond a maximum, calculated flexion point (e.g., breaking point). Thus, the support ring 202 may limit the portion of the sapphire structure 100 that deflects to the area within the support ring. Essentially, the support ring 202 may define an outer bound of an area of the sapphire structure that can flex or otherwise deform during a testing procedure and/or while under force exerted by the substantially curved contact surface 206 of contact component 204.

Moveable contact component 204 may also define a cylindrical portion 210 adjacent the substantially curved contact surface 206. Cylindrical portion 210 may be coupled to and/or partly house contact portion 208 Like contact portion 208, cylindrical portion 210 may be substantially cylindrical and/or round, and may be substantially concentric with support ring 202 and/or sapphire structure 100. As shown in FIG. 2A, cylindrical portion 210 may have a diameter (D) substantially similar or equal to the diameter of contact portion 208 and/or substantially curved contact surface 206. As discussed herein, diameter (D) of cylindrical portion 210 may be substantially similar or equal to the diameter of contact portion 208 to ensure that cylindrical portion 210 does not interfere with the material testing process performed on sapphire structure 100.

The testing process performed using testing apparatus 200, discussed briefly now and in detail below, includes stressing or otherwise applying a force to sapphire structure 100 to analyze physical and/or mechanical properties of sapphire structure 100. In a non-limiting example, sapphire structure 100 may be placed on and/or supported by support ring 202, and moveable contact component 204 of material testing apparatus 200 may move toward sapphire structure 100 and support ring 202 to initially contact, and subsequently deflect, sapphire structure 100 during the testing process. After the initial contact, sapphire structure 100 may deflect in response to moveable contact component 204 exerting force on sapphire structure 100. As discussed herein, moveable contact component 204 may exert force on sapphire structure 100 until sapphire structure 100 is deflected to and/or beyond a calculated flexion distance. The area or region of the sapphire structure that flexes may be defined or otherwise limited by the size and shape of the support ring/structure 202, as mentioned above. The calculated flexion distance may be a predetermined distance or threshold in which sapphire structure 100 may be deflected without breaking, and is dependent on the specific compositional and/or physical characteristics of sapphire structure 100 undergoing the testing process discussed herein.

This testing process may determine if sapphire structure 100 meets a predetermined quality control standard and/or may determine if sapphire structure 100 includes material defects, as similarly discussed herein with respect to FIG. 1, that may negatively affect the physical and/or mechanical properties (e.g., reduced strength) of sapphire structure 100. In a non-limiting example, and discussed herein, sapphire structure 100 may be deflected to the calculated flexion distance by testing apparatus 200 during the testing process to determine if sapphire structure meets the predetermined quality control standards. In the non-limiting example, if sapphire structure 100 does not break when deflected to the calculated flexion distance, sapphire structure 100 may be further processed to form individual components for various electronic devices, as discussed herein. However, if sapphire structure 100 does break before being deflected to the calculated flexion distance, sapphire structure 100 may require further processing to meet the predetermined quality control standard, and subsequently used within an electronic device. Alternatively, it may be determined that sapphire structure 100 may not meet the predetermined quality control standard, and may be repurposed, discarded, destroyed and/or recycled.

In another non-limiting example, the force applied to the sapphire structure 100 by moveable contact component 204 of material testing apparatus 200 may deflect sapphire structure 100 beyond the calculated flexion distance for sapphire structure 100, to intentionally break and/or attempt to break sapphire structure 100. This testing process may determine the overall maximum strength of sapphire structure 100. Additionally, the testing process may determine if sapphire structure 100 includes material defects that negatively affect the physical and/or mechanical properties of sapphire structure 100 by comparing an actual breaking deflection with a predetermined breakage deflection, as discussed herein. The predetermined breakage deflection may be a calculated and/or determinable deflection of sapphire structure 100 that may result in sapphire structure 100 breaking, shattering or cracking beyond repair. Similar to the calculated flexion distance, the predetermined breakage deflection is dependent on the specific compositional and/or physical characteristics of sapphire structure 100 undergoing the testing process discussed herein. If the sapphire structure 100 deflects beyond the calculated flexion distance, as discussed above, and/or any predetermined breakage deflection without damage, then sapphire structure 100 meets the applicable quality control standard and may be further processed to form individual components for various electronic devices, as discussed herein.

Figure 3A:
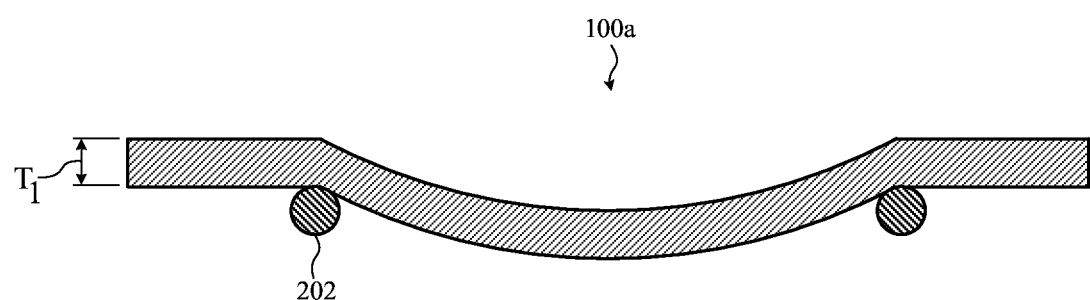
FIG. 3A depicts a side view of the sapphire structure of FIG. 1 deflected to a maximum, calculated flexion point, according to embodiments.
Figure 3B:
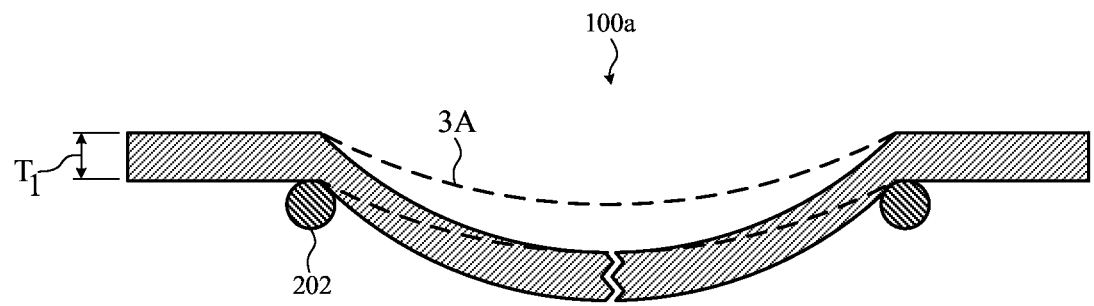
FIG. 3B depicts a side view of the sapphire structure of FIG. 1 deflected beyond a maximum, calculated flexion point, according to embodiments.
Figure 4A:
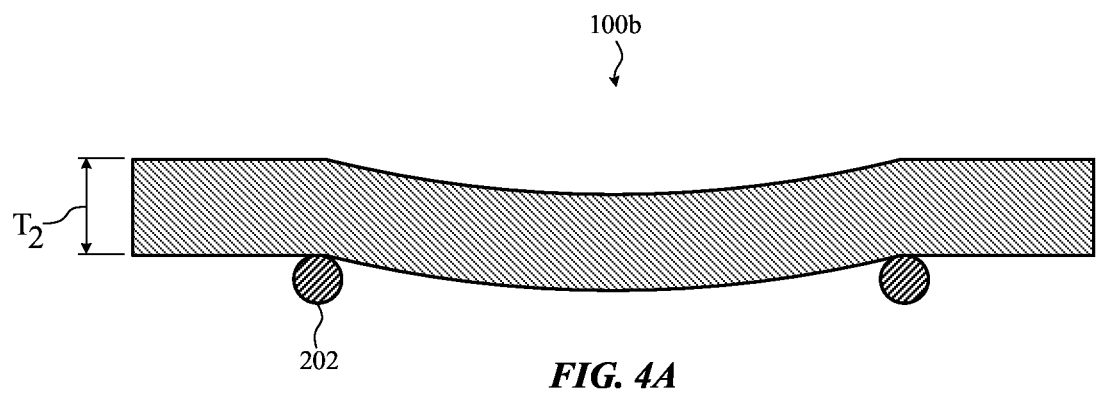
FIG.4A depicts a side view of the sapphire structure of FIG. 1 deflected to a maximum, calculated flexion point, according to additional embodiments.
Figure 4B:
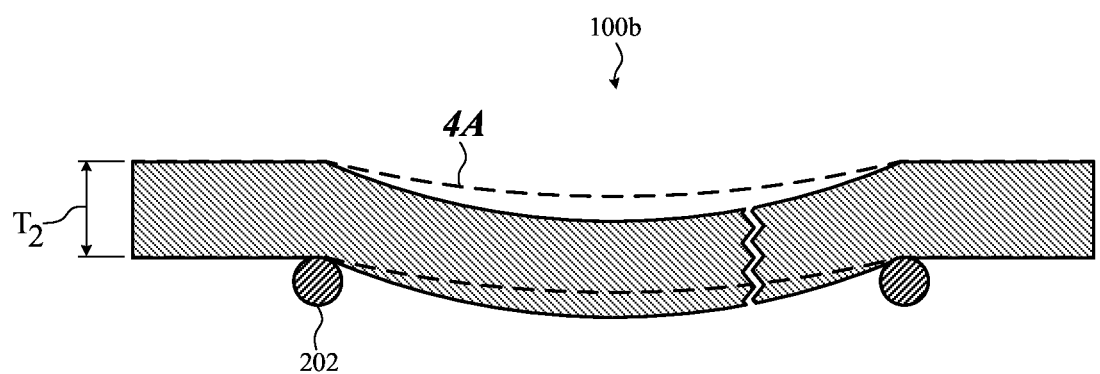
FIG. 4B depicts a side view of the sapphire structure of FIG. 1 deflected beyond a maximum, calculated flexion point, according to additional embodiments.

As discussed above, calculated flexion distances and/or predetermined breakage deflections may be specific and/or dependent on the compositional and/or physical characteristics of sapphire structure 100 undergoing the testing process. As a result, different sapphire structures 100 may include different calculated flexion distances and/or different predetermined breakage deflections. In non-limiting examples shown in FIGS. 3A and 4A, two distinct sapphire structures 100a, 100b are deflected to a calculated flexion distance. In additional non-limiting examples, FIGS. 3B and 4B show the two distinct sapphire structures 100a, 100b initially depicted in FIGS. 3A and 4A, respectively, deflected beyond the calculated flexion distance to a predetermined breakage deflection. As discussed in detail below, and shown in comparing the sapphire structures 100a, 100b shown in FIGS. 3A-4B, the calculated flexion distances and/or predetermined breakage deflections for each sapphire structure may be directly dependent on the compositional and/or physical characteristics of sapphire structure 100 undergoing the testing process discussed herein.

The difference between the calculated flexion distance in distinct sapphire structures 100a, 100b, may be based on, at least in part, the dimensions of sapphire structures 100a, 100b. In the non-limiting examples shown in FIGS. 3A and 4A, sapphire structure 100a may have a first thickness ($T_1$), and sapphire structure 100b may have a second thickness ($T_2$), where the second thickness ($T_2$) of sapphire structure 100b is greater than the first thickness ($T_1$) of sapphire structure 100a. In comparing FIGS. 3A and 4A, the larger thickness of sapphire structure 100b (see, FIG. 4A) may result in sapphire structure 100b having a smaller calculated flexion distance than sapphire structure 100a (see, FIG. 3A). As a result, sapphire structure 100a may be deflected a greater distance than sapphire structure 100b before reaching the calculated flexion distance as a result of sapphire structure 100b having a larger thickness than sapphire structure 100a.

Comparing FIGS. 3B and 4B, the larger thickness of sapphire structure 100b (see, FIG. 4B) may result in sapphire structure 100b also having a smaller predetermined breakage deflection, which is beyond the calculated flexion distance, than sapphire structure 100a (see, FIG. 3B). As a result, sapphire structure 100b may be deflected a smaller distance beyond the calculated flexion distance than sapphire structure 100a before sapphire structure 100b reaches the predetermined breakage deflection and sapphire structure 100b breaks. For reference, the calculated flexion distance for sapphire structures 100a, 100b, as illustrated in FIGS. 3A and 4A, are shown in phantom in FIGS. 3B and 4B, respectively.

Additionally in comparing FIGS. 3B and 4B, positions of a crack or break formed in sapphire structures 100a, 100b when sapphire structures 100a, 100b are deflected beyond calculated flexion distances and/or to the predetermined breakage deflections may be formed in distinct areas. In the non-limiting examples, the crack or break formed in sapphire structures 100a may be substantially in the center of sapphire structures 100a, while by comparison, the crack or break formed in sapphire structures 100b may be substantially off center. By performing the testing process discussed herein and deflecting sapphire structures 100a, 100b beyond the calculated flexion distances and/or to the predetermined breakage deflections, the position of the crack or break may indicate preexisting defects in the sapphire structures. In the non-limiting example shown in FIG. 3B where the crack or break is formed substantially in the center of sapphire structure 100a, it may be determined that the force applied by the testing apparatus 200 was experienced evenly by all portions of sapphire structure 100a, which included uniform strength and/or compositional integrity (e.g., no defects). Distinctly, where the crack or break is formed substantially in the center of sapphire structure 100b shown in FIG. 4B, it may be determined that the force applied by the testing apparatus 200 was experienced evenly by all portions of sapphire structure 100b, but the material strength of sapphire structure 100b was not uniform and/or irregularities (e.g., no defects) existed in sapphire structure 100b. In the non-limiting example, sapphire structure 100b may have included a defect in the area surround the crack or break, and as a result, the defect would have decreased the strength of sapphire structure 100b in that area, causing the crack or defect to form substantially off center when performing the testing process discussed herein.

Although discussed herein with respect to dimensions (e.g., thicknesses) of sapphire structure 100, other features of sapphire structure 100 may differentiate and/or vary the calculated flexion distance between distinct sapphire structures. In a non-limiting example, additional processes performed on sapphire structure 100 prior to undergoing a testing process using material testing apparatus 200 may vary the calculated flexion distance and the predetermined breakage deflection. For example, sapphire structure 100 may be annealed prior to being tested; the annealed structure may have a distinct calculated flexion distance and predetermined breakage deflection when compared to a sapphire structure 100 of similar dimensions that may not have undergone an annealing process prior to the material testing.

As discussed herein, the calculated flexion distance for sapphire structure 100 may be calculated to determine the force necessary to deflect sapphire structure 100 to analyze physical and/or mechanical properties of sapphire structure 100. The calculation of the calculated flexion distance for sapphire structure 100 may be based on a variety of characteristics for sapphire structure 100. In non-limiting examples, specific material characteristics and physical characteristics of sapphire structure 100 may be utilized in calculating the calculated flexion distance for sapphire structure. Material characteristics of sapphire structure 100 may include material composition of sapphire structure 100, young's modulus of the material forming sapphire structure 100 and/or pre-testing processes performed on sapphire structure 100 (e.g., annealing). Physical characteristics of sapphire structure 100 may include a thickness of sapphire structure 100, a dimension (e.g., width, circumference) of sapphire structure 100 and/or a dimension of a desired testing area of sapphire material 100, among other characteristics.

The calculation of the calculated flexion distance for sapphire structure 100 may also be based on a variety of physical characteristics of material testing apparatus 200. In non-limiting examples, the physical characteristics may be based on characteristics of support ring 202, including but not limited to, the dimensions (e.g., diameter) of support ring 202 and/or the dimension of a contact area formed between the support ring and sapphire structure 100, insofar as support ring 202 may define (or help define) an area of the sapphire substrate subject to flexion and another area that is not subject to flexion, namely the portion of the substrate outside the ring.

Figure 5:
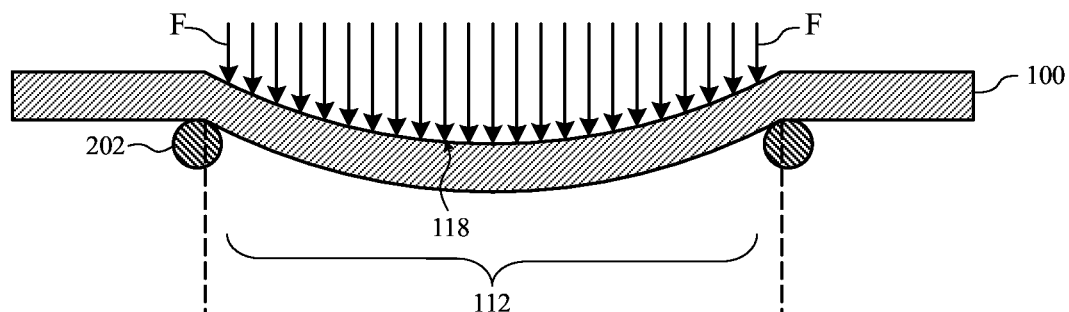
FIG. 5 depicts a calculated force profile required to deflect the sapphire structure of FIG. 1 to the maximum, calculated flexion point depicted in FIG. 3A, according to embodiments.

Utilizing the various characteristics of sapphire structure 100 and/or material testing apparatus 200, the deflection required to reach the calculated flexion distance for sapphire structure 100 may be determined. Additionally, a required force that must be implemented on sapphire structure 100 to achieve the calculated flexion distance may also be determined. As shown in FIG. 5, the force required to deflect sapphire structure 100 to the calculated flexion distance may be continuously applied to sapphire structure 100 between support ring 202, such that an entire test area 112 of sapphire structure 100 positioned between and/or aligned within the inner edge of support ring 202 of material testing apparatus 200 may experience a force (F). Additionally, to achieve the calculated flexion distance for sapphire structure 100, the magnitude of the force (F) applied in test area 112 varies. In a non-limiting example, the magnitude of the force (F) applied to test area 112 of sapphire structure 100 increases as the distance from the support ring 202 increases. The force (F) applied to test area is represented by an array of arrows; two of which are labeled "F." It is understood that the number and/or size of the array of arrows representing the force or set of forces (F) applied to sapphire structure 100 is merely exemplary for showing a varying force (or set of forces) applied to test area 112, and is not necessarily depicted to scale either absolutely or relative to one another.

By calculating the calculated flexion distance, and calculating the force required to deflect sapphire structure 100 to the calculated flexion distance and applying the force (F) over the entire test area 112 of sapphire structure 100, a deflection-force profile 118 for sapphire structure 100 may also be determined. The deflection-force profile 118 may represent the shape or curvature of test area 112 of sapphire structure 100 when it is flexed to the calculated flexion distance.

In another non-limiting example, a set of forces to be applied to test area 112 of sapphire structure 100 can be calculated. That is, rather than determining deflection-force profile 118 for sapphire structure 100 based on the calculated flexion distance for sapphire structure 100, a set of forces can be calculated. The calculated set of forces can include the specific magnitude of forces to be applied in specific portions of test area 112 of sapphire structure 100 to deflect sapphire structure 100 to the calculated flexion distance.

As discussed herein, test area 112 of sapphire structure 100 may be positioned between and/or aligned within the inner edge of support ring 202 of material testing apparatus 200. That is, test area 112 of sapphire structure 100 may be defined by the size and/or diameter of support ring 202. In non-limiting examples, test area 112 may occupy only a portion of sapphire structure 100, or alternatively, may be substantially the entire surface of sapphire structure 100. As a result of test area 112 being variable in size and/or dependent on the size of support ring 202, testing apparatus 200 may be capable of testing and/or applying a force to varying areas of sapphire structure 100.

Figure 6:
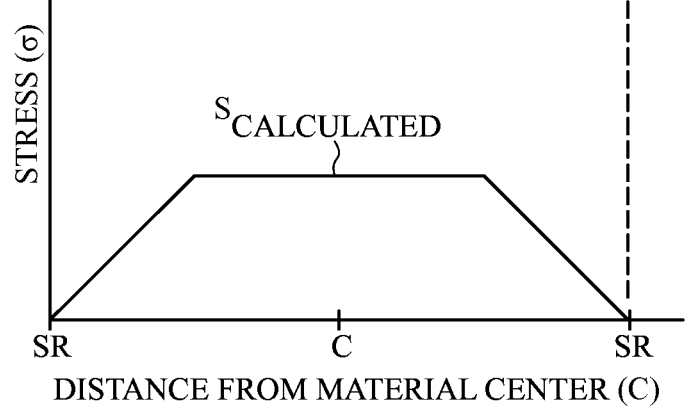
FIG. 6 depicts a stress-graph illustrating the uniform, calculated stress applied to the sapphire structure of FIG. 1 when a calculated force profile is applied to deflect the sapphire structure to a maximum, calculated flexion point as shown in FIG. 5, according to embodiments.

FIG. 6 is a stress graph illustrating the calculated stress (σ) applied to and/or experienced by test area 112 of sapphire structure 100 to deflect sapphire structure 100 to the calculated flexion distance as shown and discussed herein with respect to FIG. 5. As shown in FIG. 6, label "SR" represents a distance at which support ring 202 touches the structure 100. More specifically with comparison to FIG. 5, SR represents points at which support ring 202 touches or supports sapphire structure 100, such that the structure is not deflected outside of the test area 112. Additionally, label "C" of FIG. 6 represents the a point equating to a center of test area 112 of sapphire structure 100.

The stress graph shown in FIG. 6 is the calculated or ideal stress (a) experienced by sapphire structure 100 to deflect sapphire structure to the calculated flexion distance. As a result, the stress graph in FIG. 6 is a representation of a perfect test structure and operation of the testing process discussed herein. Additionally as discussed herein, a stress graph indicating the actual stress experienced by sapphire structure 100 may be similar, but not identical to the stress graph shown in FIG. 6.

As shown in FIG. 6, at least some portion of a calculated stress ($S_{calculated}$) is being uniformly applied to or experienced by sapphire structure 100 in at least a portion of test area 112 defined between support ring 202 of material testing apparatus 200. That is, and as shown in FIG. 6, the calculated stress ($S_{calculated}$) may be substantially uniform or consistent in a centralized portion of test area 112 of sapphire structure 100. The uniform calculated stress ($S_{calculated}$) as shown in FIG. 6 may be substantially centered on center (C) of test area 112 and may be positioned between SR points or the portion of support ring 202 where sapphire structure 100 is completely supported by support ring 202, as discussed above. The calculated stress ($S_{calculated}$) distribution to sapphire structure 100 as shown in FIGS. 5 and 6 may be the ideal or desired stress (σ) distribution on sapphire structure 100 when deflecting sapphire structure 100 to the calculated flexion distance, as discussed herein.

Figure 7:
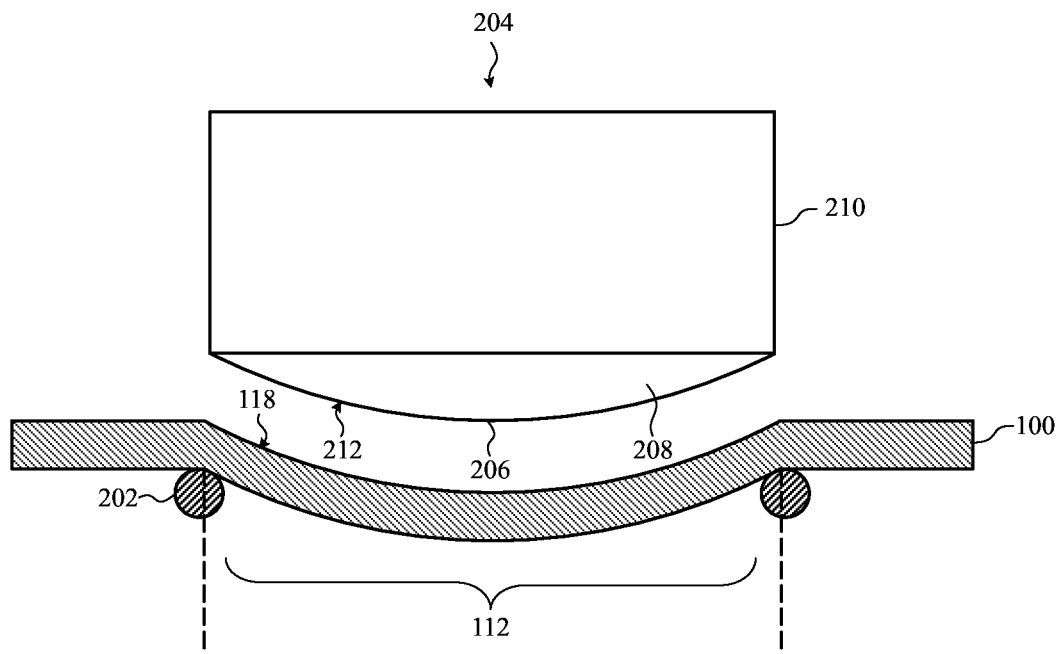
FIG. 7 depicts a side view of a moveable contact component of a material testing apparatus having a substantially curved contact surface and the sapphire structure of FIG. 5, according to embodiments.

In order to achieve the ideal or desired stress distribution (e.g., substantially uniform stress) across the test area 112 of sapphire structure 100 when deflecting sapphire structure 100 to the calculated flexion distance, substantially curved contact surface 206 of moveable contact component 204 may include a curvature profile 212. As shown in FIG. 7, curvature profile 212 of substantially curved contact surface 206 may be identical or substantially similar to the deflection-force profile 118 of sapphire structure 100. Curvature profile 212 of substantially curved contact surface 206 may be identical or substantially similar to the deflection-force profile 118 of sapphire structure 100 to ensure sapphire structure 100 is deflected identically, or as close as possible, to deflection-force profile 118; which is the ideal curvature that matches the calculated flexion distance for sapphire structure 100, as discussed herein. This specific shape or curvature (e.g., curvature profile 212) for curved contact surface 206 allows testing apparatus 200 to obtain accurate testing of sapphire structure 100, discussed herein with respect to FIGS. 7 and 8.

As similarly discussed herein with respect to FIG. 5, curvature profile 212 of substantially curved contact surface 206 of moveable contact component 204 may be based on material characteristics (e.g., material composition, young's modulus, pre-testing processes and so on) and/or physical characteristics (e.g., thickness, dimension, testing area dimension and so on) of sapphire structure 100. Additionally, curvature profile 212 of substantially curved contact surface 206 may be based on physical characteristics of material testing apparatus 200, and specifically, physical characteristics of support ring 202 (e.g., diameter, dimension of a contact area formed between support ring 202 and sapphire structure 100 and so on).

In addition to being based, at least in part, on the characteristics of sapphire structure 100 and/or support ring 202 of material testing apparatus 200, curvature profile 212 of substantially curved contact surface 206 may also be based on the testing process performed on sapphire structure 100. In non-limiting examples, curvature profile 212 of substantially curved contact surface 206 may be based on whether sapphire structure 100 is being deflected to the calculated flexion distance, or alternatively, beyond the calculated flexion distance to the predetermined breakage deflection, as discussed herein with respect to FIGS. 3A and 3B. As discussed herein, curvature profile 212 may vary radially between a center and a perimeter of substantially curved contact surface 206, where the variations and/or distinct curvature regions in the curvature profile 212 may contact distinct portions of sapphire structure 100 during the distinct testing processes performed on sapphire structure 100.

Figure 8:
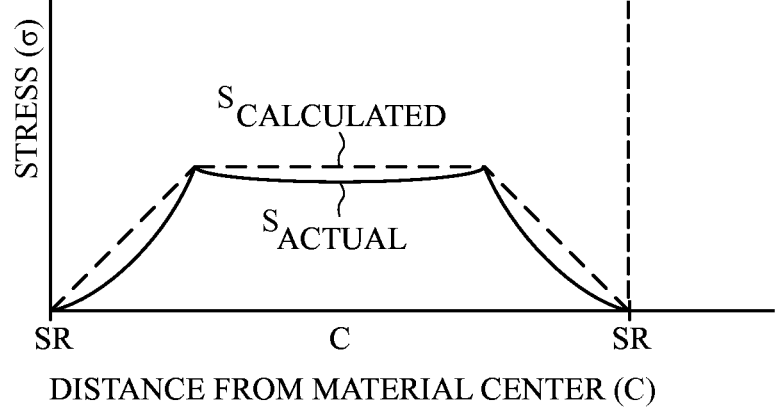
FIG. 8 depicts a stress-graph illustrating the actual stress experienced by the sapphire structure of FIG. 1 to deflect the sapphire structure to a maximum, calculated flexion point as shown in FIG. 7, according to embodiments.

FIG. 8 shows a stress-graph illustrating the actual stress (a) applied to or experienced by test area 112 of sapphire structure 100, by substantially curved contact surface 206 having curvature profile 212. Additionally, FIG. 8 shows in phantom the calculated stress (a) for test area 112 of sapphire structure 100 as discussed herein with respect to FIG. 6. It is understood that the reference markings or indicators (e.g., SR, C) shown in stress-graph of FIG. 8 are substantially similar to those depicted in stress-graph of FIG. 6. As such, the reference markings shown in FIG. 8 represent similar distances of support ring 202 and/or sapphire structure 100, as discussed herein with respect to FIG. 6. Redundant explanation of these reference markings is omitted for clarity.

In comparison, by forming substantially curved contact surface 206 to have curvature profile 212 that may be substantially identical to deflection-force profile 118 of sapphire structure 100, the actual stress ($S_{actual}$) exerted onto sapphire structure 100 may be substantially similar to the calculated stress ($S_{calculated}$) and/or may also be substantially uniform. Although the actual stress ($S_{actual}$) is shown in FIG. 8 to slightly vary from the calculated stress ($S_{calculated}$), it is understood that the difference between the actual stress ($S_{actual}$) and the calculated stress ($S_{calculated}$) is often slight, inconsequential, negligible and/or unavoidable. The differences between the actual stress ($S_{actual}$) and the calculated stress ($S_{calculated}$) may be a result of inconsistencies or variations in the testing environment (e.g., ambient temperature or pressure), variations in the testing material (e.g., material temperature, surface defects and/or undetectable thickness discrepancies), and/or variations in material testing apparatus (e.g., slight variations in the radii of curved contact surface 206 or misalignment of moveable contact component 204 and/or support ring 202). As a result of the actual stress ($S_{actual}$) and the calculated stress ($S_{calculated}$) being substantially similar, the data received when testing sapphire structure 100 to analyze physical and/or mechanical properties of sapphire structure 100 may be substantially accurate.

As discussed herein with respect to FIGS. 7 and 8, curvature profile 212 of substantially curved contact surface 206 of material testing apparatus 200 is identical or near-identical to a deflection-force profile 118 for sapphire structure 100. Additionally as discussed herein with respect to FIGS. 3A-4B, sapphire structures 100 may have varying calculated flexion distances dependent on characteristics of sapphire structure 100. Because the deflection-force profile 118 is directly dependent on the calculated flexion distances, the deflection-force profile 118 for various, distinct sapphire structures 100 may also vary. As a result, curvature profile 212 of substantially curved contact surface 206 may also vary dependent on sapphire structure 100. That is, contact portion 208 having curvature profile 212 may be interchangeable and/or may be modified to correspond to distinct sapphire structures 100 having distinct deflection-force profiles 118.

Figure 9:
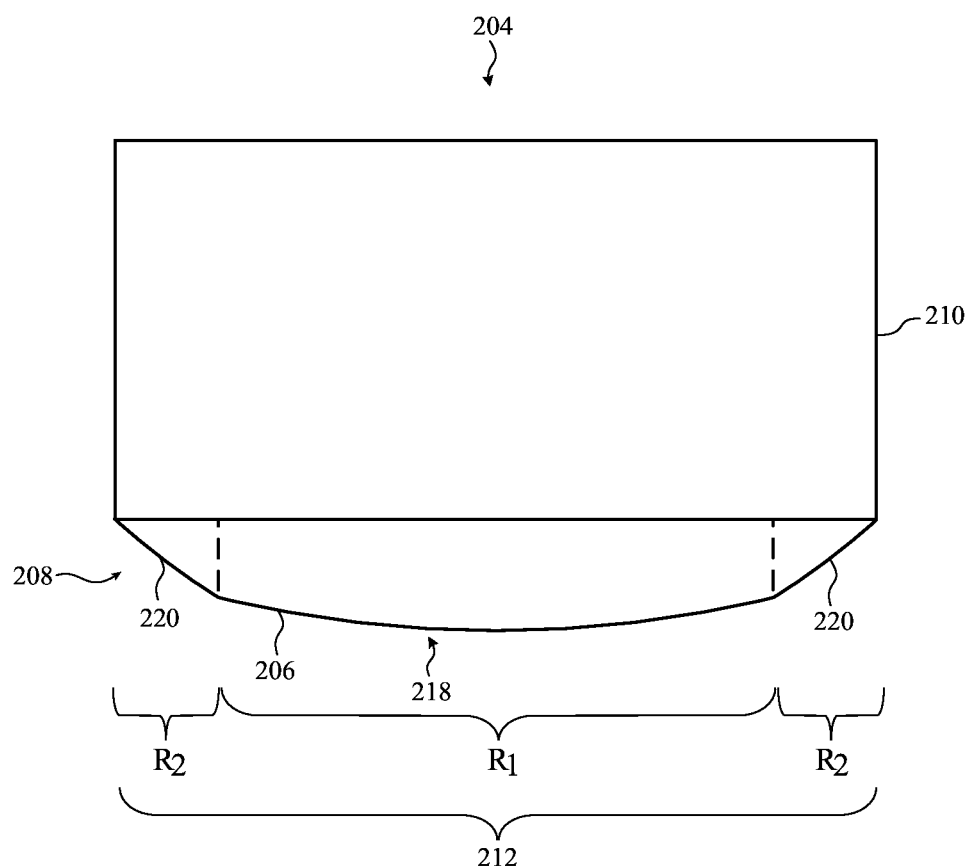
FIG. 9 depicts a side view of a moveable contact component of a material testing apparatus having a substantially curved contact surface, according to embodiments.
Figure 10:
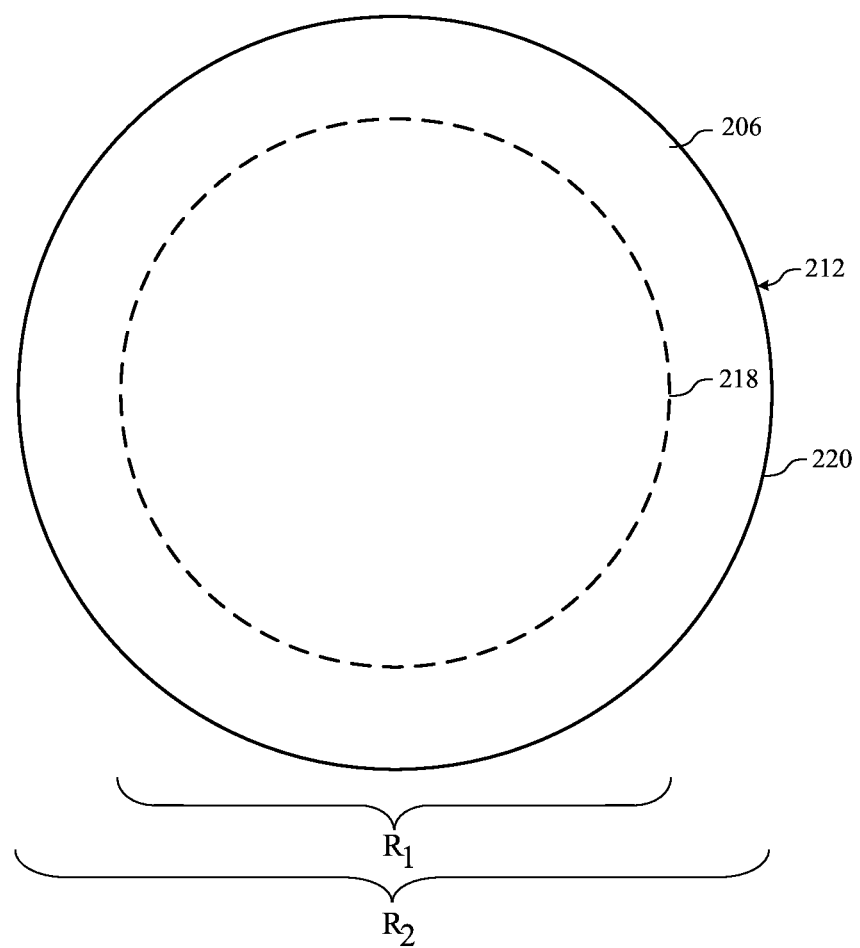
FIG. 10 depicts a bottom view of the moveable contact component of the material testing apparatus of FIG. 9, according to embodiments.
Figure 11:
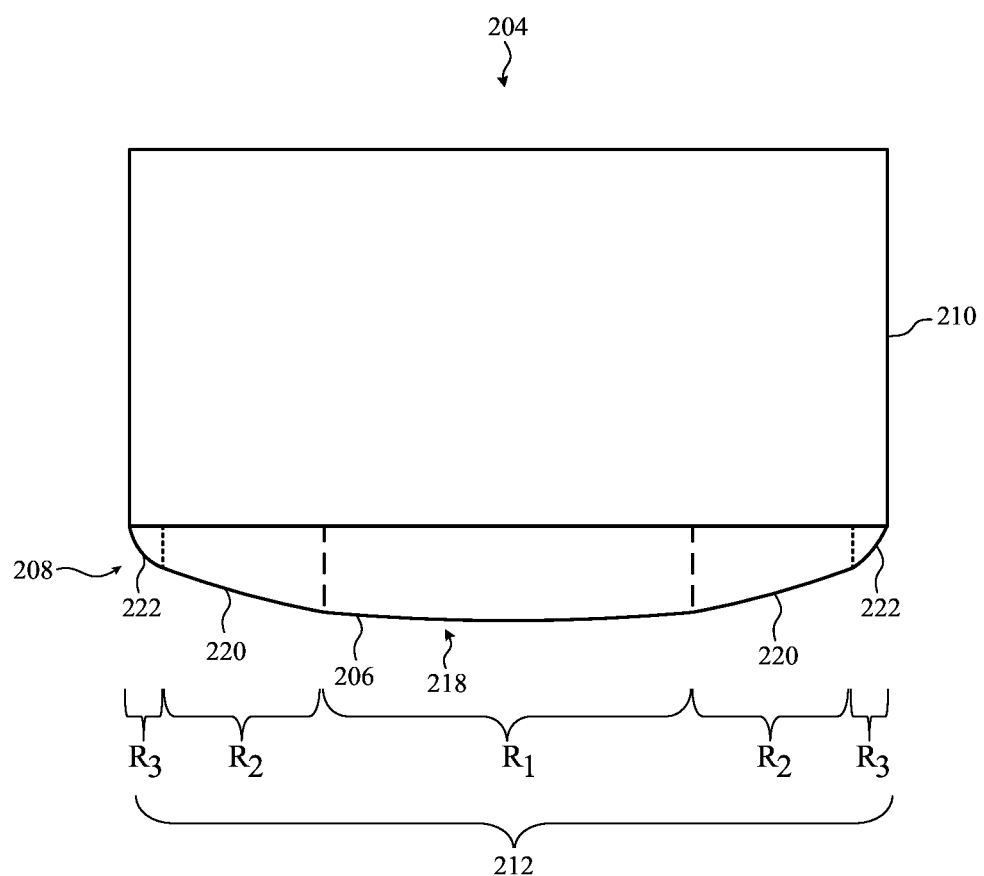
FIG. 11 depicts a side view of a moveable contact component of a material testing apparatus having a substantially curved contact surface, according to embodiments.
Figure 12:
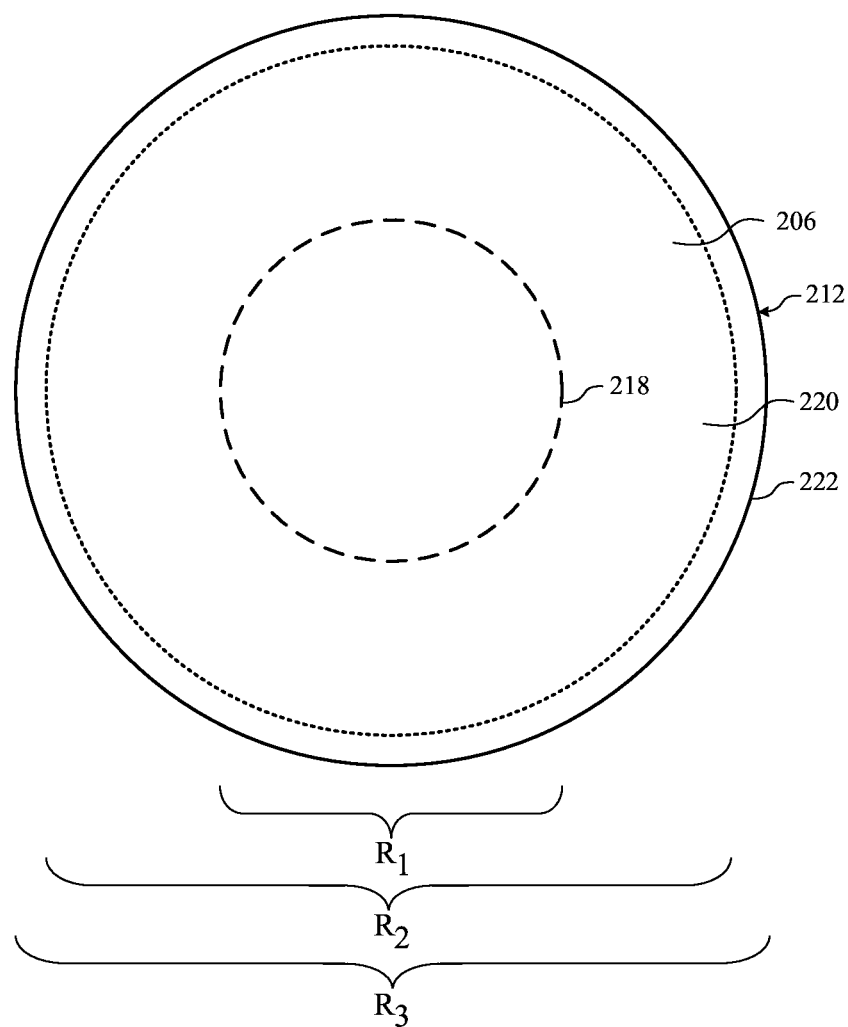
FIG. 12 depicts a bottom view of the moveable contact component of the material testing apparatus of FIG. 11, according to embodiments.

As discussed herein, curvature profile 212 may have a varying radius between a center and a perimeter of substantially curved contact surface 206. As shown in FIGS. 9 and 10, the varying radius of curvature profile 212 of contact surface 206 may include a first curved region 218 having a first curvature radius ($R_1$) and at least one distinct or second curved region 220 substantially surrounding first curved region 218. Second curved region 220 has a second curvature radius ($R_2$) that may be distinct from the first curvature radius ($R_1$) of first curved region 218. In a non-limiting example shown in FIG. 9, second curvature radius ($R_2$) of second curved region 220 may be less than first curvature radius ($R_1$) of first curved region 218.

Each of the curved regions 218, 220 of substantially curved contact surface 206 may contact sapphire structure 100 during specific testing processes, as discussed herein. In a non-limiting example, and as discussed in detail herein with respect to FIGS. 14A-14F, first curved region 218 may contact sapphire structure 100 when sapphire structure 100 is deflected to the calculated flexion distance and when sapphire structure 100 is deflected beyond the calculated flexion distance. Additionally in the non-limiting example, and as discussed herein with respect to FIGS. 14A-14F, second curved region 220 may contact sapphire structure 100 only when sapphire structure 100 is deflected beyond the calculated flexion distance and/or to the predetermined breakage deflection. The variations in the curvature radii may ensure that sapphire structure 100 is being contacted by substantially all of curved contact surface 206 when sapphire structure 100 is undergoing a material testing process, as discussed herein.

Similar to FIGS. 9 and 10, FIGS. 11 and 12 show another non-limiting example of moveable contact component 204. In the non-limiting example shown in FIGS. 11 and 12, substantially curved contact surface 206 has a curvature profile 212 of varying radius, defining first curved region 218, second curved region 220 substantially surrounding first curved region 218 and a third curved region 222 substantially surrounding first curved region 218 and second curved region 220. As similarly discussed herein, the distinct curved regions 218, 220, 222 formed on substantially curved contact surface 206 may include distinct curvature radii ($R_{1-3}$) that may contact distinct portions of sapphire structure 100 during material testing processes.

Figure 13:
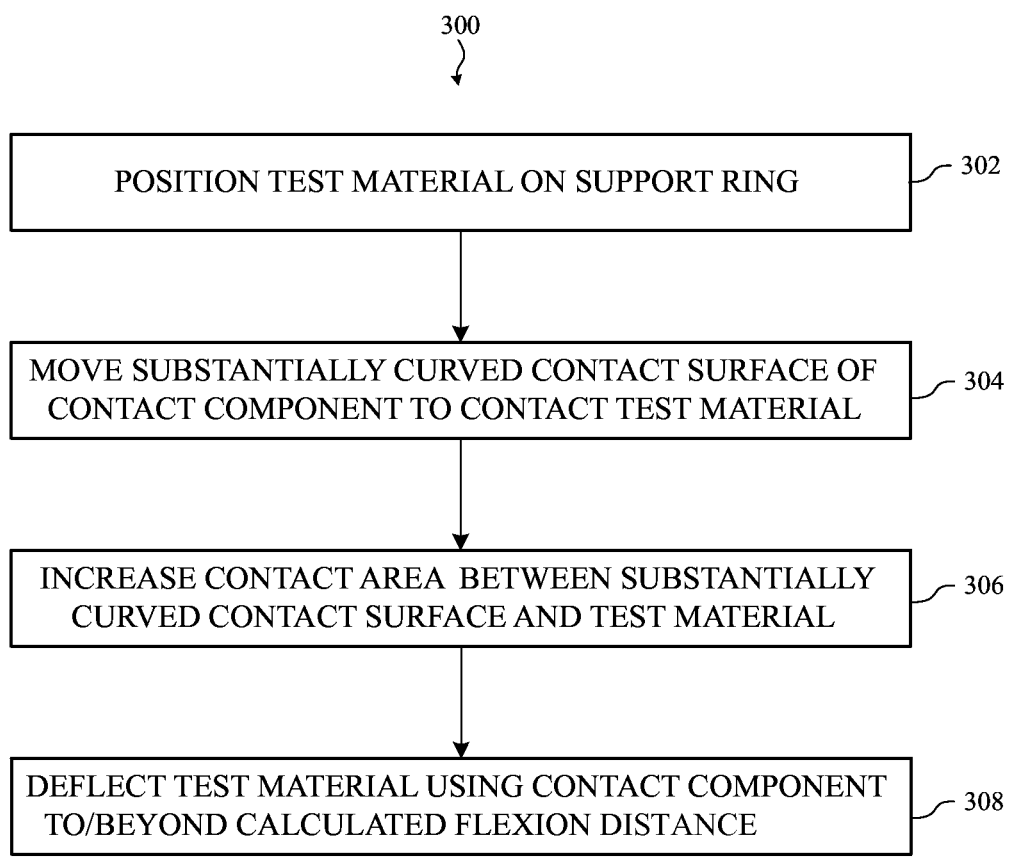
FIG. 13 depicts a flow chart of an example process for testing a sapphire structure, according to embodiments.

FIG. 13 depicts an example process for testing a sapphire structure. Specifically, FIG. 13 is a flowchart depicting one example process 300 for stressing or deflecting a sapphire structure to analyze physical and/or mechanical properties of the stressed sapphire structure In operation 302, a test material (e.g., sapphire structure) is positioned on a support ring of a material testing apparatus. The sapphire structure is positioned on the support ring and is also positioned between the support ring and a moveable contact component of the material testing apparatus. Once positioned on the support ring, the sapphire structure is substantially stationary and may not be displaced.

In operation 304, the contact component of the material testing apparatus is moved toward the sapphire structure and the support ring. The contact component moves toward the sapphire structure to contact a substantially curved contact surface of the contact component to the sapphire structure. The substantially curved contact surface of the contact component includes a curvature profile based on a deflection-force profile for the sapphire structure. The deflection-force profile is based on, at least in part, material and/or physical characteristics of the sapphire structure and/or physical characteristics of the support ring of the material testing apparatus.

In operation 306, the contact area increases between the substantially curved contact surface of the contact component and the sapphire structure. The increasing of the contact area also includes continuously moving the contact component toward the sapphire structure and the support ring and increasing and/or distributing a force or set of forces applied to the sapphire structure using the contact component. Additionally, the increasing of the contact area includes an increase in a uniform stress area formed on the sapphire structure.

In operation 308, the contact component deflects the sapphire structure. Specifically, the sapphire structure is deflected to a calculated flexion distance for the sapphire structure and/or beyond the calculated flexion distance to a predetermined breakage deflection. If the sapphire structure breaks prior to being deflected to the calculated flexion distance, the sapphire structure is presumed to include material defects, and as such, may not meet criteria to be implemented in an electronic device. However, if the sapphire structure does not break or breaks after being deflected beyond the calculated flexion distance, the sapphire structure includes the desired physical and/or mechanical properties necessary to be implemented in an electronic device.

FIGS. 14A-14F show multiple views of sapphire structure 100 undergoing the process 300 discussed herein with respect to FIG. 13. As shown in FIGS. 14A-14F, and as similarly discussed herein with respect to FIGS. 9 and 10, substantially curved contact surface 206 having curvature profile 212 may include a first curved region 218 having a first curvature radius ($R_1$), and at least one distinct or second curved region 220 substantially surrounding first curved region 218. Second curved region 220 has a second curvature radius ($R_2$) that may be distinct from the first curvature radius ($R_1$) of first curved region 218. In a non-limiting example shown in FIG. 9, second curvature radius ($R_2$) of second curved region 220 may be less than first curvature radius ($R_1$) of first curved region 218.

Figure 14A:
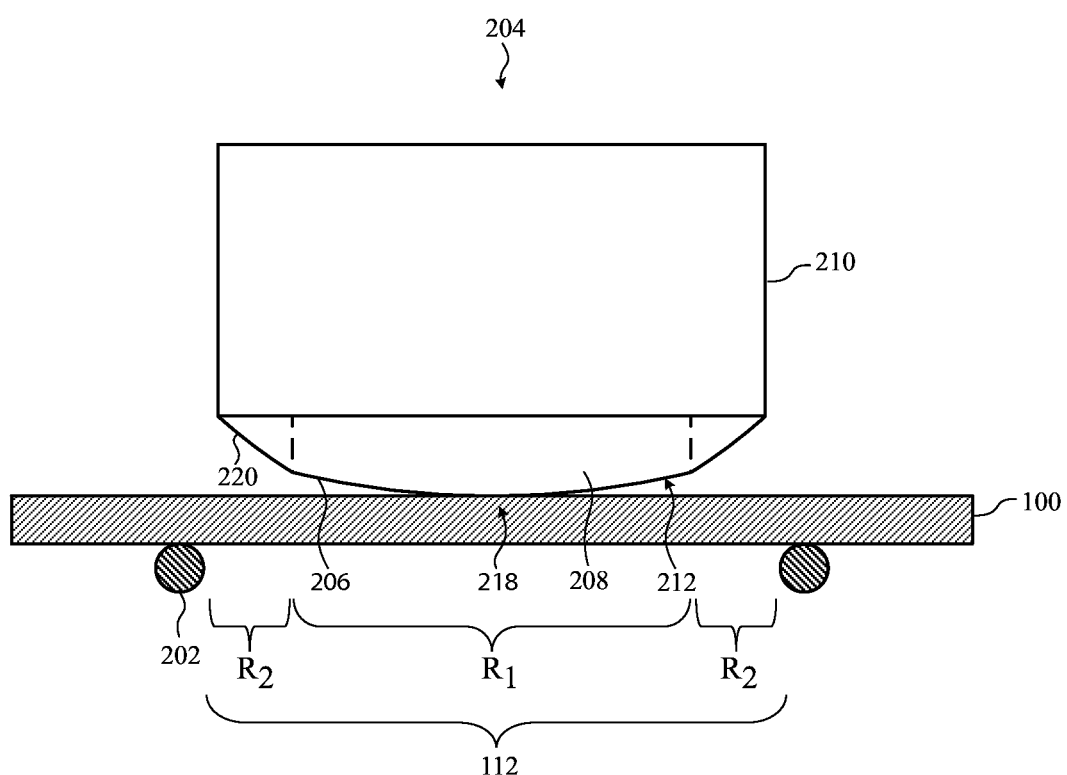
FIG. 14A shows a side view of a material testing apparatus and a sapphire structure undergoing a portion of the process of FIG. 13, according to embodiments.
Figure 14B:
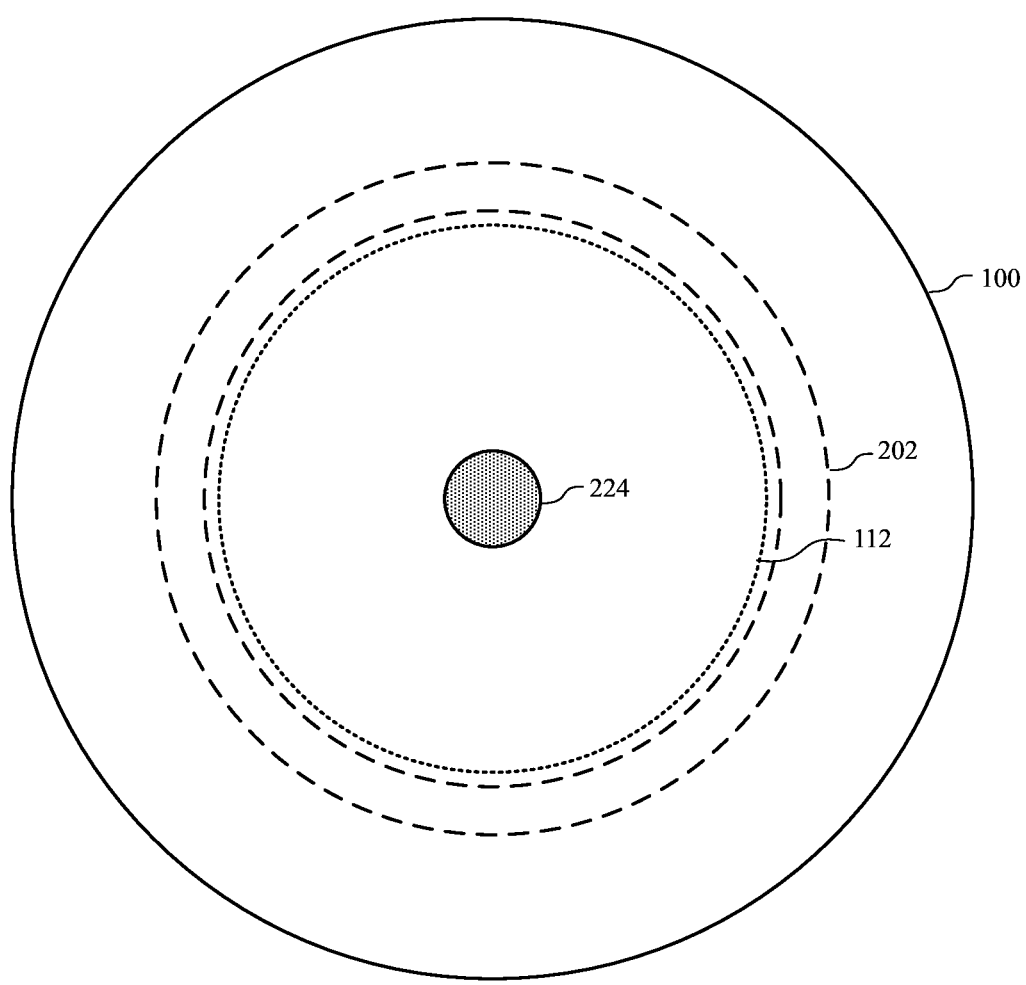
FIG. 14B shows a top view of the sapphire structure of FIG. 14A including a contact area formed on a top surface of the sapphire structure by the moveable contact component of the material testing apparatus, according to embodiments.

FIG. 14A shows a side view of substantially curved contact surface 206 initially contacting sapphire structure 100. Contact component 204 of material testing apparatus 200 may not yet deflect sapphire structure 100 through support ring 202, as discussed herein. As shown in FIGS. 14A and 14B, only a portion of first curved region 218 having first curvature radius ($R_1$) is contacting sapphire structure 100. As a result, and as shown in the top view of sapphire structure 100 in FIG. 14B, contact area 224 formed between substantially curved contact surface 206 and sapphire structure 100 may be substantially small and may only occupy a portion of test area 112, shown in phantom, of sapphire structure 100. FIGS. 14A and 14B may correspond to operations 302 and 304 of process 300 shown in FIG. 13. Although shown as only occupying a portion of sapphire structure 100, it is understood that test area 112 may be substantially the entire surface of sapphire structure 100. That is, and as discussed herein with respect to FIGS. 5 and 6, test area 112 may be defined by the portion of sapphire structure 100 that may be positioned between and/or in alignment with the inner boundaries of support ring 202 of testing apparatus 200. As such, test area 112 of sapphire structure 100 may increase as the size and/or diameter of support ring 202 also increases.

Figure 14C:
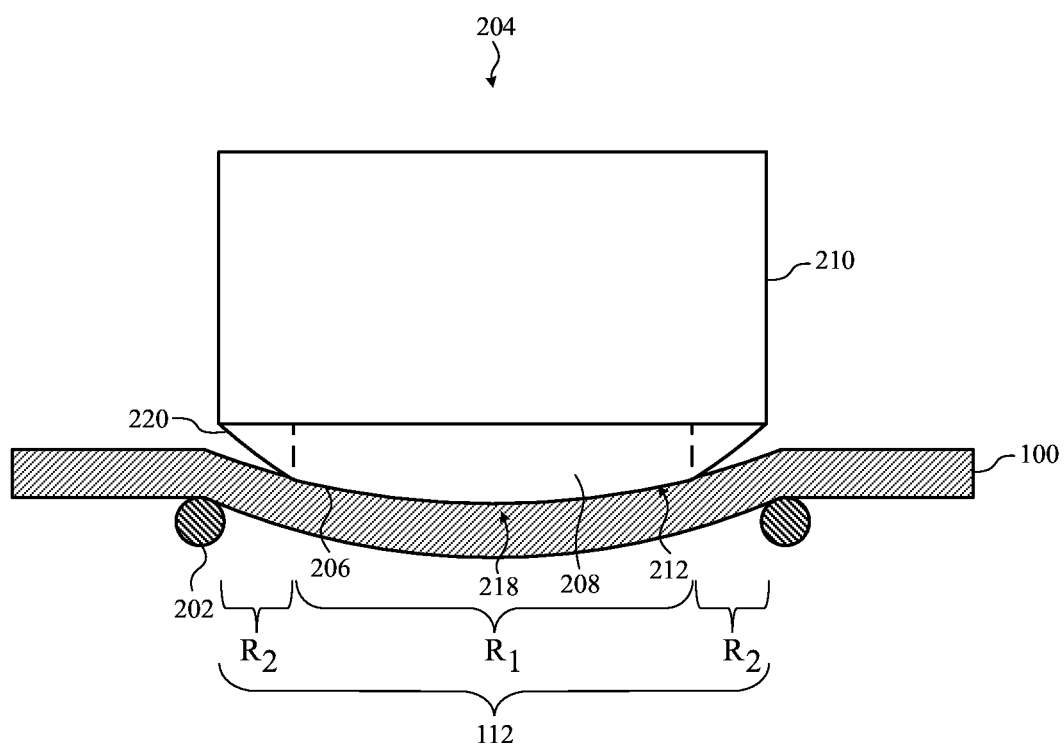
FIG. 14C shows a side view of the material testing apparatus and the sapphire structure of FIG. 14A undergoing a portion of the process of FIG. 13, according to embodiments.

FIG. 14C shows a side view of contact component 204 moving toward sapphire structure 100 in order to exert force thereon, such that sapphire structure 100 may deflect. In the non-limiting example, contact component 204 continuously moves toward sapphire structure 100 such that substantially curved contact surface 206 contacts sapphire structure 100 to deflect sapphire structure to a calculated flexion distance. As shown in FIG. 14C, when sapphire structure 100 is deflected to the calculated flexion distance, the entire first curved region 218 having first curvature radius ($R_1$) of substantially curved contact surface 206 may be in contact with sapphire structure 100. Additionally, because sapphire structure 100 is only deflected to the calculated flexion distance, second curved region 220 of substantially curved contact surface 206 may not contact sapphire structure 100. Furthermore, the portion or region of sapphire structure 100 that is contacted by first curved region 218 of substantially curved contact surface 206 may include or assume, (under testing) a curvature, displacement or flexion identical to substantially curved contact surface 206 having the first curved region 218.

Figure 14D:
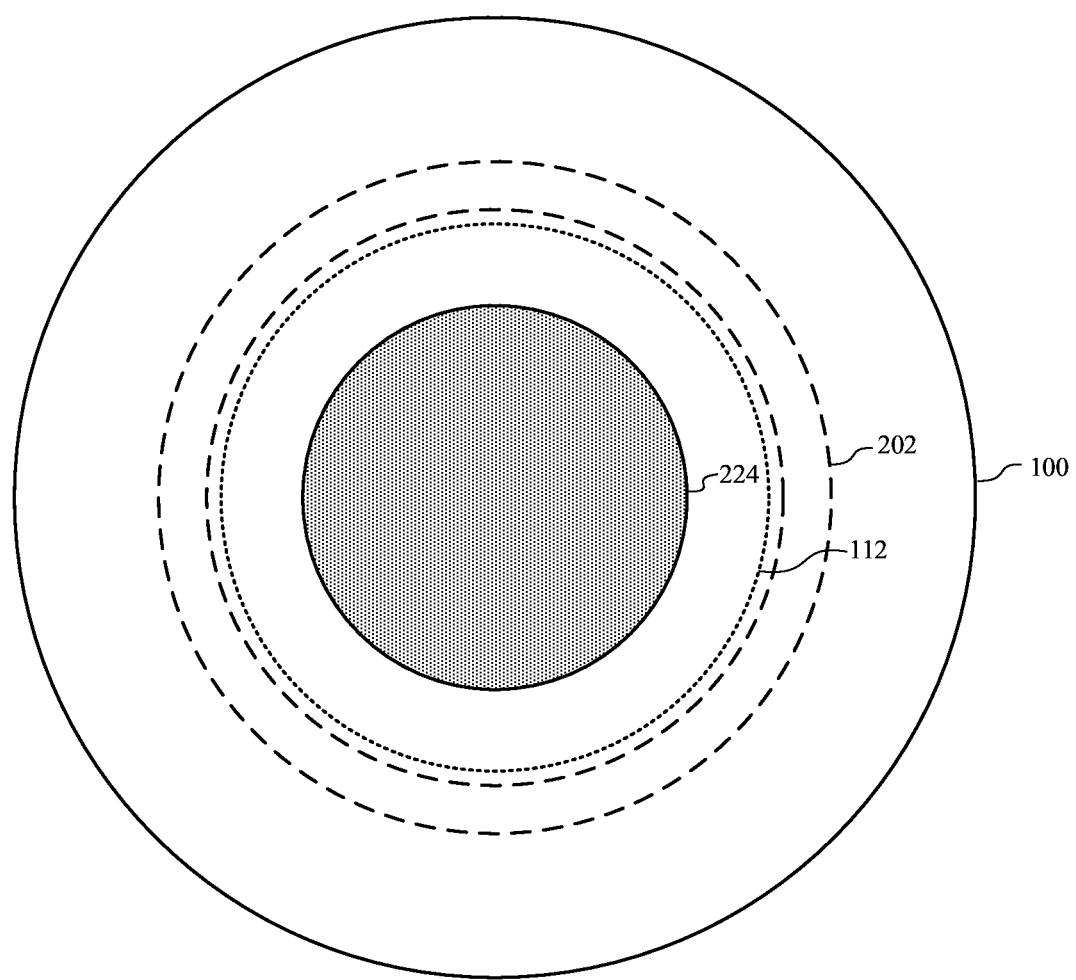
FIG. 14D shows a top view of the sapphire structure of FIG. 14C including a contact area formed on a top surface of the sapphire structure by the moveable contact component of the material testing apparatus, according to embodiments.

Turning to FIG. 14D, and with comparison to FIG. 14B, contact area 224 between substantially curved contact surface 206 of contact component 204 and sapphire structure 100 may increase. In the non-limiting example, and as discussed above with respect to FIG. 14C, as sapphire structure 100 is deflected to the calculated flexion distance more of first curved region 218 of substantially curved contact surface 206 may contact sapphire structure 100, thus increasing the contact area 224. Although contact area 224 has increased when sapphire structure 100 is deflected to the calculated flexion distance, contact area 224 may still only occupy a portion of test area 112 of sapphire structure 100. As contact area 224 increases, a force applied to sapphire structure 100 via moveable contact component 204 may also increase. Additionally, as contact area 224 increases, a uniform stress area applied to sapphire structure 100 may also increase. FIGS. 14C and 14D may correspond to operations 304, 306 and 308 of process 300 shown in FIG. 13.

Figure 14E:
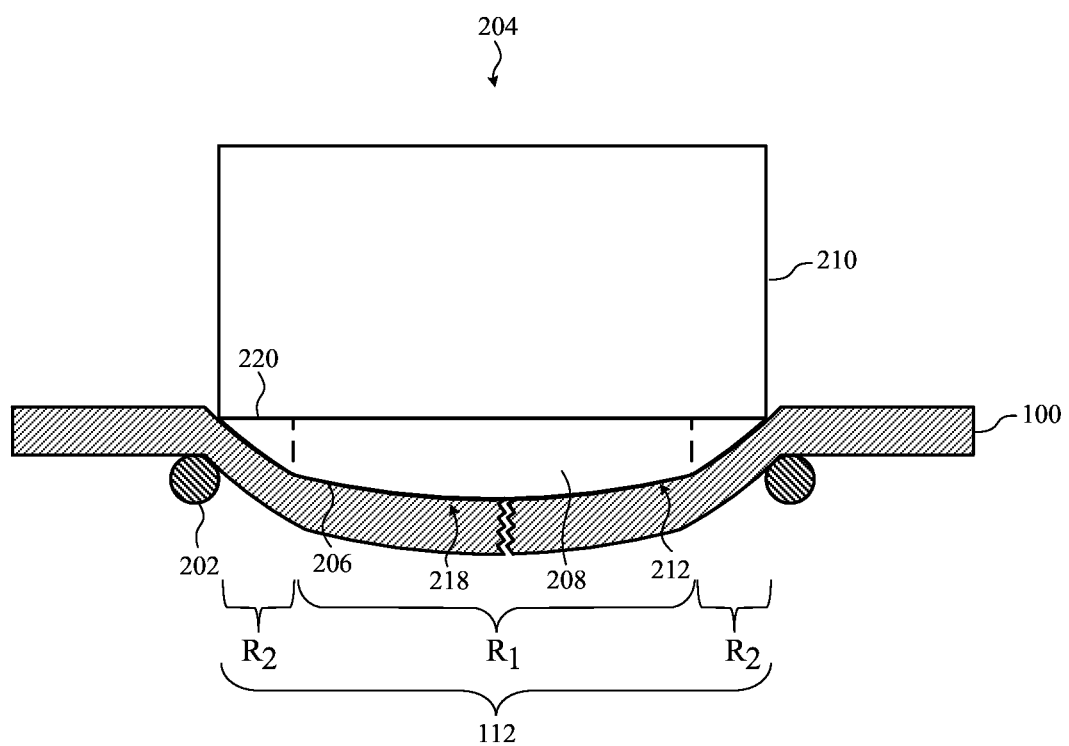
FIG. 14E shows a side view of the material testing apparatus and the sapphire structure of FIG. 14A undergoing a portion of the process of FIG. 13, according to embodiments.

FIG. 14E shows contact component 204 impacting and/or exerting force on sapphire structure 100, such that sapphire structure 100 may deflect to a predetermined breakage deflection. In the non-limiting example, contact component 204 may be moved toward sapphire structure 100 such that substantially curved contact surface 206 contacts sapphire structure 100 to deflect sapphire structure beyond the calculated flexion distance to cause sapphire structure 100 to break. As shown in FIG. 14E, when sapphire structure 100 is deflected beyond the calculated flexion distance, the entire first curved region 218 having first curvature radius ($R_1$) of substantially curved contact surface may be in contact with sapphire structure 100. Additionally, when sapphire structure 100 is deflected beyond the calculated flexion distance, second curved region 220 of substantially curved contact surface 206 may also contact sapphire structure 100.

Figure 14F:
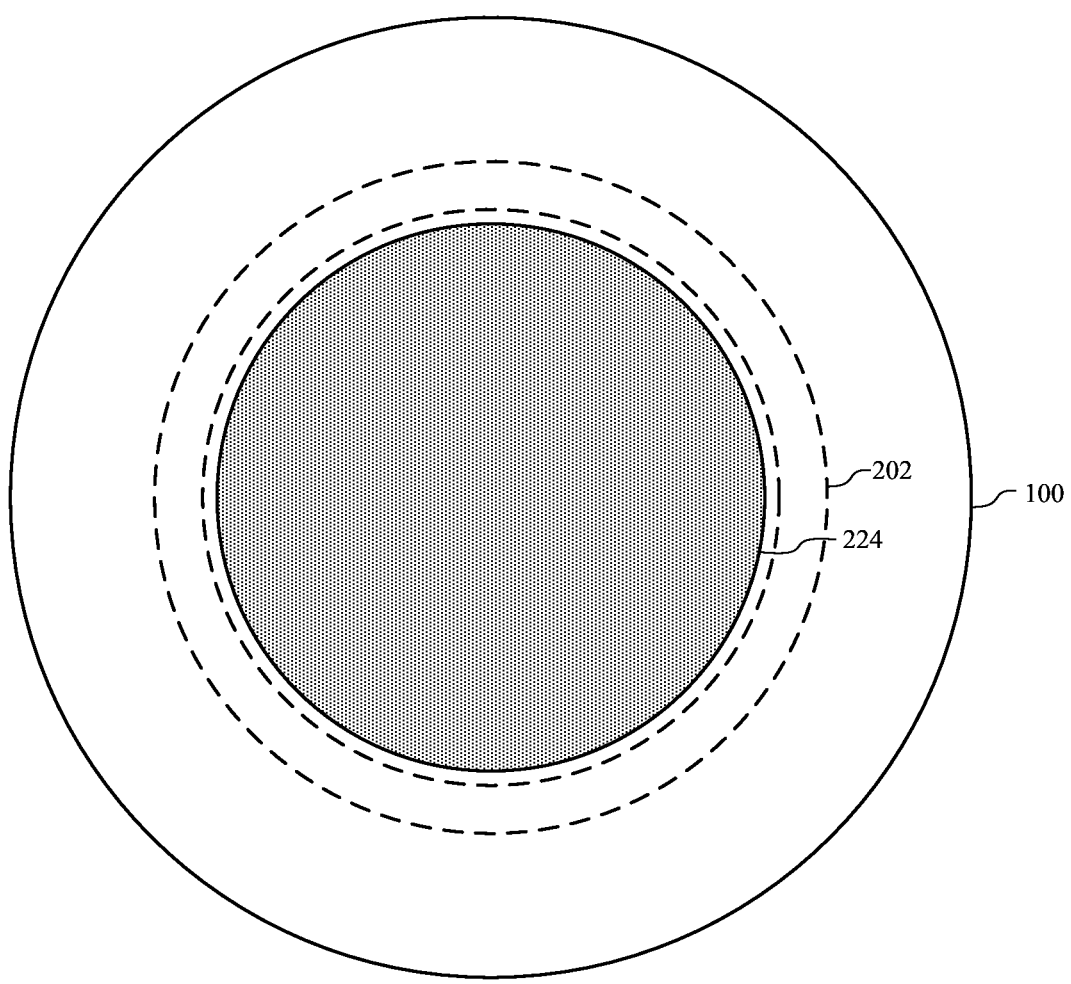
FIG. 14F shows a top view of the sapphire structure of FIG. 14E including a contact area formed on a top surface of the sapphire structure by the moveable contact component of the material testing apparatus, according to embodiments.

As shown in FIG. 14F, and with comparison to FIGS. 14B and 14D, contact area 224 between substantially curved contact surface 206 of contact component 204 and sapphire structure 100 may increase to the size of test area 112 of sapphire structure 100. In the non-limiting example, and as discussed above with respect to FIG. 14E, as sapphire structure 100 is deflected beyond the calculated flexion distance all of first curved region 218 and second curved region 220 of substantially curved contact surface 206 may contact sapphire structure 100, thus increasing the contact area 224. FIGS. 14E and 14F may correspond to operations 304, 306 and 308 of process 300 shown in FIG. 13.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A material testing apparatus, comprising:
a support ring adjacent a sapphire test material; and
a moveable contact component positioned adjacent the support ring and comprising:
a substantially curved contact surface defined by a curvature profile of varying radius formed between a center and a perimeter of the substantially curved contact surface, wherein
the moveable contact component is configured to deflect the sapphire test material into an aperture of the ring.

2. The material testing apparatus of claim 1, wherein the substantially curved contact surface contacts the sapphire test material on a side opposite the support ring.

3. The material testing apparatus of claim 1, wherein the substantially curved contact surface further comprises:
a first curved region having a first curvature radius; and
a second curved region substantially surrounding the first curved region, and having a second curvature radius different from the first curvature radius of the first curved region.

4. The material testing apparatus of claim 3, wherein the second curvature radius of the second curved region is less than the first curvature radius of the first curved region.

5. The material testing apparatus of claim 3, wherein the first curved region contacts the sapphire test material in response to:
deflecting the sapphire test material to a calculated flexion distance for the test material; and
deflecting the sapphire test material beyond the calculated flexion distance for the test material.

6. The material testing apparatus of claim 5, wherein the second curved region contacts the sapphire test material in response to deflecting the sapphire test material beyond the calculated flexion distance for the sapphire test material.

7. The material testing apparatus of claim 1, wherein the moveable contact component further comprises a cylindrical portion positioned adjacent the substantially curved contact surface.

8. The material testing apparatus of claim 1, wherein the substantially curved contact surface has a diameter equal to or smaller than an inner diameter of the support ring.

9. A material testing apparatus, comprising:
a support ring operative to support a first side of a sapphire test material; and
a moveable contact component operative to contact a second side of the sapphire test material and comprising
a contact surface having a curvature profile of varying radius, configured to contact the test material when a predetermined force is exerted on the sapphire test material by the moveable contact component, wherein
the sapphire test material is subject to flex within the support ring when the predetermined force is applied.

10. The material testing apparatus of claim 9, wherein a contact surface has a curvature profile of varying radius that comprises:
a first region configured to contact the second side of the sapphire test material when a first force is exerted by the moveable contact component on the sapphire test material; and
a second region surrounding the first region and configured to contact the second side of the sapphire test material when a second force is exerted by the moveable contact component on the sapphire test material.

11. The material testing apparatus of claim 10, wherein:
the first force is less than the second force; and
the second region does not contact the second side of the sapphire test material when the first force is exerted by the moveable contact component on the sapphire test material.

12. The material testing apparatus of claim 10, wherein the support ring defines a test area contacted by the second region when the second force is exerted on the sapphire test material.

13. The material testing apparatus of claim 12, wherein the test area is substantially the entire second surface of the sapphire test material.

14. The material testing apparatus of claim 9, wherein the support ring delineates a boundary between a first region of the sapphire test material subject to flex when the first force is applied and a second region of the sapphire test material that is not subject to flex when the first force is applied.

15. The material testing apparatus of claim 14, wherein the first region of the sapphire test material defines a curvature identical to the contact surface having the curvature profile of the varying radius when the first force is applied.

16. A method for testing a sapphire test material, the method comprising:
positioning a sapphire test material on a support ring of a material testing apparatus;
moving a contact component of the material testing apparatus toward the sapphire test material to contact a substantially curved contact surface of the contact component to the sapphire test material, the substantially curved contact surface comprising a variably curved curvature profile ; and
deflecting the sapphire test material by pressing the contact component into the sapphire test material, wherein the sapphire test material deflects to one of:
a calculated flexion distance for the sapphire test material, or
beyond the calculated flexion distance for the sapphire test material.

17. The method of claim 16, wherein deflecting the sapphire test material comprises generating a substantially uniform stress in the sapphire test material.

18. The method of claim 17, wherein generating the substantially uniform stress comprises substantially uniformly stressing a test area of the sapphire test material defined by the support ring of the material testing apparatus.

19. The method of claim 17, wherein deflecting the sapphire test material further comprises at least one of:
continuously moving the contact component toward the sapphire test material and the support ring;
increasing a force applied to the sapphire test material via the contact component; and
increasing an area of the uniform stress generated in the sapphire test material.

20. The method of claim 16, wherein:
the method further comprises determining the deflection-force profile for the sapphire test material based on at least one of:
material characteristics of the sapphire test material;
physical characteristics of the sapphire test material; or
physical characteristics of the support ring; and
the curvature profile is based on the determined deflection-force profile for the sapphire test material.

21. The method of claim 20, wherein the substantially curved contact surface further comprises:
  a first curved portion having a first curvature radius; and
  a second curved portion substantially surrounding the first curved portion, the second curved portion having a second curvature radius different from the first curvature radius of the first curved portion.

22. The method of claim 21, wherein:
  the first curved portion contacts the sapphire test material in response to deflecting the sapphire test material to the calculated flexion distance for the sapphire test material; and
  the second curved portion contacts the sapphire test material in response to deflecting the sapphire test material beyond the calculated flexion distance for the sapphire test material.

* * * * *